(12) United States Patent
Jaiswal et al.

(10) Patent No.: US 12,354,752 B2
(45) Date of Patent: Jul. 8, 2025

(54) METHOD AND SYSTEM FOR EARLY DETECTION OF COVID-19

(71) Applicant: Tata Consultancy Services Limited, Mumbai (IN)

(72) Inventors: Dibyanshu Jaiswal, Kolkata (IN); Shakil Ahmad, Bangalore (IN); Mithun Basaralu Sheshachala, Bangalore (IN); Kartik Muralidharan, Bangalore (IN); Arpan Pal, Kolkata (IN); Ramesh Kumar Ramakrishnan, Bangalore (IN); Balakumar Kanagasabapathy, Chennai (IN); Tanmay Acharia, Kolkata (IN); Loknath Tiwari, Kolkata (IN); Kayapanda Mandana, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 232 days.

(21) Appl. No.: 18/346,717

(22) Filed: Jul. 3, 2023

(65) Prior Publication Data
US 2024/0013918 A1   Jan. 11, 2024

(30) Foreign Application Priority Data
Jul. 8, 2022   (IN) .............................. 202221039456

(51) Int. Cl.
*G16H 50/20* (2018.01)
*G16H 40/67* (2018.01)
*A61B 5/024* (2006.01)

(52) U.S. Cl.
CPC ............. *G16H 50/20* (2018.01); *G16H 40/67* (2018.01); *A61B 5/02416* (2013.01); *A61B 5/02438* (2013.01)

(58) Field of Classification Search
CPC .... G16H 50/20; G16H 40/67; A61B 5/02416; A61B 5/02438
See application file for complete search history.

(56) References Cited

U.S. PATENT DOCUMENTS

| 8,337,404 | B2 * | 12/2012 | Osorio ............... A61B 5/14539 |
| | | | 600/301 |
| 9,460,557 | B1 * | 10/2016 | Tran ......................... G06T 17/20 |

(Continued)

FOREIGN PATENT DOCUMENTS

WO   WO2021231044   11/2021

OTHER PUBLICATIONS

Conroy, Nature, 2022, pp. 1-12.*

(Continued)

*Primary Examiner* — Michael I Ezewoko
(74) *Attorney, Agent, or Firm* — Finnegan, Henderson, Farabow, Garrett & Dunner, LLP

(57) ABSTRACT

The present invention relates to a method and system for early detection of COVID-19. Existing methods require data from multiple sensors for training a prediction model whose output is considered as final prediction which is actually the prediction for a particular day or time instance. However, this prediction doesn't detect actual infection of COVID-19 since it requires monitoring the change in health of the user over consecutive days. Embodiments of present disclosure overcome these challenges by a prediction model for COVID-19 which requires only data from Photoplethysmography (PPG) sensor seamlessly collected from a wearable device still able to provide accurate COVID-19 prediction with application of a post processing technique on the predictions of the prediction model. Since COVID-19 symptoms have an effect on heartrate and oxygen saturation which are effectively captured by PPG sensor data, studying (Continued)

these dynamics during infection period gives insights to perform early detection of COVID-19.

3 Claims, 6 Drawing Sheets

(56) References Cited

U.S. PATENT DOCUMENTS

| | | | | |
|---|---|---|---|---|
| 10,799,186 | B2* | 10/2020 | Howard | A61B 5/11 |
| 11,266,855 | B2* | 3/2022 | Enwemeka | A61N 5/0603 |
| 2012/0083700 | A1* | 4/2012 | Osorio | A61B 5/7264 |
| | | | | 600/483 |
| 2014/0330408 | A1* | 11/2014 | Rolley | G16H 10/60 |
| | | | | 700/91 |
| 2017/0251985 | A1* | 9/2017 | Howard | A61B 5/0077 |
| 2019/0108912 | A1* | 4/2019 | Spurlock, III | A61P 25/28 |
| 2019/0110754 | A1* | 4/2019 | Rao | G06N 7/00 |
| 2020/0107733 | A1* | 4/2020 | Valys | A61B 5/7282 |
| 2020/0222718 | A1* | 7/2020 | Enwemeka | A61M 16/0666 |
| 2023/0229939 | A1* | 7/2023 | Straehle | G06N 7/01 |
| | | | | 706/46 |
| 2023/0290506 | A1* | 9/2023 | Jarayaman | G16H 50/30 |
| 2024/0249848 | A1* | 7/2024 | Solmaz | G16H 50/30 |

OTHER PUBLICATIONS

Conroy, Bryan et al., "Real-time infection prediction with wearable physiological monitoring and AI to aid military workforce readiness during COVID-19", Title of the item: Scientific Reports, Date: 2022, Publisher: Nature, Link: https:/ /www.nature.com/articles/s41598-022-07764-6.pdf.

Rae Cho, Hyeong et al., "Machine learning-based optimization of pre-symptomatic COVID-19 detection through smartwatch", Title of the item: Scientific Reports, Date: 2022, Publisher: Nature, Link: https://www.nature.com/articles/s41598-022-11329-y.pdf.

D'Haese, Pierre-François et al., "Prediction of viral symptoms using wearable technology and artificial intelligence: A pilot study in healthcare workers", Title of the item: Plos One, Date: 2021, Publisher: D'Haese, Link: https://journals.plos.org/plosone/article?id=10.1371/journal.pone.0257997.

* cited by examiner

METHOD AND SYSTEM FOR EARLY DETECTION OF COVID-19

PRIORITY CLAIM

This U.S. patent application claims priority under 35 U.S.C. § 119 to: Indian Patent Application No. 202221039456, filed on Jul. 8, 2022. The entire contents of the aforementioned application are incorporated herein by reference.

TECHNICAL FIELD

The present invention generally relates to the field of disease detection based on data collected from a wearable device and, more particularly, to method and system for early detection of COVID-19 by post processing output of a prediction model trained to predict COVID-19.

BACKGROUND

Currently there is one doctor for every 1,445 Indians as per the country's current population estimate of 1.35 billion, which is lower than the World Health Organization's (WHO's) prescribed norm of one doctor for 1,000 people. This shortage of doctors (and nurses) coupled with the fact that frontline health care workers are most likely to be exposed to coronavirus than anybody else, makes protecting them critical. Recently a study using two years of Fitbit data from nearly 50,000 users found that wearable data could accurately predict local flu outbreaks than the standard system used by the Centers for Disease Control and Prevention. Some other works show how self-reporting and wearable data can act complementary to virus testing. Since coronavirus disease (COVID-19) and the seasonal flu have some common symptoms, it is possible to develop an Artificial Intelligence (AI) based early warning system using physiological data collected from wearable devices. Such a system could help predict the onset of symptoms and identify whether a health care worker might have been infected with the virus and thus assist in timely action. Also, it gives confidence to frontline health care workers that they are healthy and continuously being monitored for risk.

Since health care workers use Personal Protective Equipment (PPE kits), they cannot carry any personal devices like mobile phones or subject themselves to frequent data capture using standard clinical measurement devices like thermometer, pulse oximeter etc. Also, any Wi-Fi or Bluetooth based data transmissions could interfere with Intensive Care Unit (ICU) electronics, therefore any real time data transmission has to be avoided. Existing AI based early warning systems require data collected from multiple sensors such as thermometer, oximeter etc. Further, some of them collect information about symptoms from user along with data from multiple sensors to train the AI models for COVID-19 prediction. The information provided by the user may not be correct and affects the accuracy of overall prediction. Also, these systems consider output of the AI model as final prediction which is actually the prediction for a particular day or time instance. However, this prediction may not help in detecting actual infection of COVID-19 since it requires monitoring the change in health of the user over consecutive days.

SUMMARY

Embodiments of the present disclosure present technological improvements as solutions to one or more of the above-mentioned technical problems recognized by the inventors in conventional systems. For example, in one embodiment, a method for early detection of COVID-19 is provided. The method includes receiving photoplethysmography (PPG) data collected by a wearable device of a subject for a predefined time span. Further the method includes dividing the PPG data into a plurality of instances of pre-defined time windows and extracting one or more relevant features of each of the plurality of instances. The one or more relevant features are identified during training phase using a Maximal Information Coefficient (MICe) technique. The method further includes deriving predictions corresponding to each of the plurality of instances based on the one or more relevant features via a trained prediction model. The derived predictions are one of: (i) COVID positive and (ii) COVID negative. Furthermore, the method includes post-processing the derived predictions by segmenting the derived predictions into a plurality of segments in accordance with a predefined time period and computing a Positive Instance Ratio ($PIR_t$) of the derived predictions for each of the plurality of segments. The $PIR_t$ is ratio of a number COVID positive instances in a segment among the plurality of segments to a number of the plurality of instances falling within the segment. The post-processing further comprises generating a trend line ($PIR_{avg}$) from the $PIR_t$ corresponding to each of the plurality of segments by taking a moving average of pre-defined window size and determining a final prediction on whether the subject is COVID-19 positive based on comparison of the $PIR_{avg}$ with a pre-determined threshold value.

In another aspect, a system for early detection of COVID-19 is provided. The system includes: a memory storing instructions; one or more communication interfaces; and one or more hardware processors coupled to the memory via the one or more communication interfaces, wherein the one or more hardware processors are configured by the instructions to: receive photoplethysmography (PPG) data collected by a wearable device of a subject for a predefined time span. Further, the one or more hardware processors are configured to divide the PPG data into a plurality of instances of pre-defined time windows and extract one or more relevant features of each of the plurality of instances. The one or more relevant features are identified during training phase using a Maximal Information Coefficient (MICe) technique. The one or more hardware processors are further configured to derive predictions corresponding to each of the plurality of instances based on the one or more relevant features via a trained prediction model. The derived predictions are one of: (i) COVID positive and (ii) COVID negative. Furthermore, the one or more hardware processors are configured to post-process the derived predictions by segmenting the derived predictions into a plurality of segments in accordance with a predefined time period and computing a Positive Instance Ratio ($PIR_t$) of the derived predictions for each of the plurality of segments. The $PIR_t$ is ratio of a number COVID positive instances in a segment among the plurality of segments to a number of the plurality of instances falling within the segment. The post-processing further comprises generating a trend line ($PIR_{avg}$) from the $PIR_t$ corresponding to each of the plurality of segments by taking a moving average of pre-defined window size and determining a final prediction on whether the subject is COVID-19 positive based on comparison of the $PIR_{avg}$ with a pre-determined threshold value.

In yet another aspect, there are provided one or more non-transitory machine-readable information storage mediums comprising one or more instructions which when executed by one or more hardware processors cause a method for early detection of COVID-19. The method includes receiving photoplethysmography (PPG) data collected by a wearable device of a subject for a predefined time span. Further the method includes dividing the PPG data into a plurality of instances of pre-defined time windows and extracting one or more relevant features of each of the plurality of instances. The one or more relevant features are identified during training phase using a Maximal Information Coefficient (MICe) technique. The method further includes deriving predictions corresponding to each of the plurality of instances based on the one or more relevant features via a trained prediction model. The derived predictions are one of: (i) COVID positive and (ii) COVID negative. Furthermore, the method includes post-processing the derived predictions by segmenting the derived predictions into a plurality of segments in accordance with a predefined time period and computing a Positive Instance Ratio ($PIR_t$) of the derived predictions for each of the plurality of segments. The $PIR_t$ is ratio of a number COVID positive instances in a segment among the plurality of segments to a number of the plurality of instances falling within the segment. The post-processing further comprises generating a trend line ($PIR_{avg}$) from the $PIR_t$ corresponding to each of the plurality of segments by taking a moving average of pre-defined window size and determining a final prediction on whether the subject is COVID-19 positive based on comparison of the $PIR_{avg}$ with a pre-determined threshold value.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
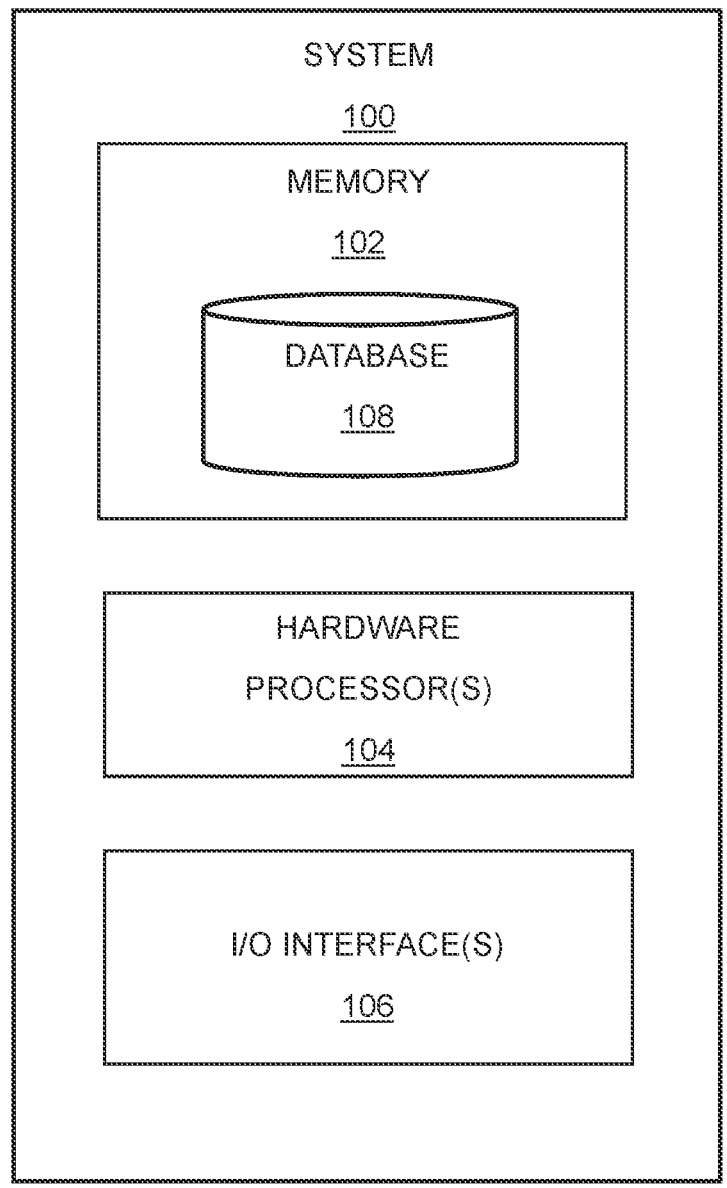
FIG. 1 illustrates an exemplary block diagram of a system for early detection of COVID-19, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Early detection of COVID-19, especially in healthcare workers, is necessary to prevent spread of the disease as well as to treat the infected people before they're severely affected. Since healthcare workers use PPE kits, they cannot carry any personal devices or subject themselves to frequent data capture using standard clinical measurement devices like thermometer, pulse-oximeter. Further, Wi-Fi or Bluetooth based data transmissions could interfere with ICU Electronics, therefore real time data transmission is challenging. Hence, embodiments of present disclosure periodically collect data internally stored in a wearable device (for example, Empatica E4) worn by a subject (for example, healthcare worker) throughout the day. The collected data is then used to predict COVID-19 using an AI based prediction model. Existing works require data from multiple sensors for training the AI based prediction models. Also, these systems consider output of the prediction model as final prediction which is actually the prediction for a particular day or time instance. However, this prediction may not help in detecting actual infection of COVID-19 since it requires monitoring the change in health of the user over consecutive days. In order to overcome these challenges, embodiments of present disclosure disclose a prediction model for COVID-19 which requires only single sensor data i.e. data from Photoplethysmography (PPG) sensor seamlessly collected from the wearable device still able to provide accurate COVID-19 prediction with application of a post processing technique on the predictions of the prediction model. Since COVID-19 symptoms have an effect on heartrate and oxygen saturation which are effectively captured by PPG sensor data, studying these dynamics during infection period gives insights to perform early detection of COVID-19. It has been experimentally identified that method of present disclosure can predict the onset of the infection trend a few days in advance of the actual clinical deterioration or classical symptoms appear using only PPG data. Although method of present disclosure has been experimented on healthcare workers, it can be used to detect COVID-19 infection in any other subjects who put on the wearable device and allow to be continuously monitored. It should also be noted that method of present disclosure is not an alternative to standard tests done for detecting COVID-19 but it helps in detection of possible infection a few days in advance of the actual clinical deterioration or classical symptoms appear. The prediction from method of present disclosure can be used to initiate a standard physical examination and Reverse Transcription-Polymerase Chain Reaction (RT-PCR) test to confirm the findings leading to early interventions and thereby avoiding clinical complications of the disease such as cytokine storm.

Referring now to the drawings, and more particularly to FIGS. 1 to 8, where similar reference characters denote corresponding features consistently throughout the figures, there are shown preferred embodiments and these embodiments are described in the context of the following exemplary system and/or method.

FIG. 1 illustrates an exemplary block diagram for early detection of COVID-19. In an embodiment, the system 100 includes one or more processors 104, communication interface device(s) 106 or Input/Output (I/O) interface(s) 106 or user interface 106, and one or more data storage devices or memory 102 operatively coupled to the one or more processors 104. The memory 102 comprises a plurality of modules (not shown) such as a prediction module for COVID-19 prediction and a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud, and the like. The system 100 is connected to one or more devices such as smart watches or similar wearable devices for PPG sensing.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) 106 receives data from wearable devices as input and provides COVID-19 prediction as output. The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The database 108 may store information but not limited to information associated with at least one of: PPG data collected from one or more wearable devices belonging to one or more subjects, trained prediction model and so on. Further, the database 108 stores information pertaining to inputs fed to the system 100 and/or outputs generated by the system (e.g., at each stage), specific to the methodology described herein. Functions of the components of system 100 are explained in conjunction with flow diagrams depicted in FIGS. 2A and 2B for early detection of COVID-19.

Figure 2A:
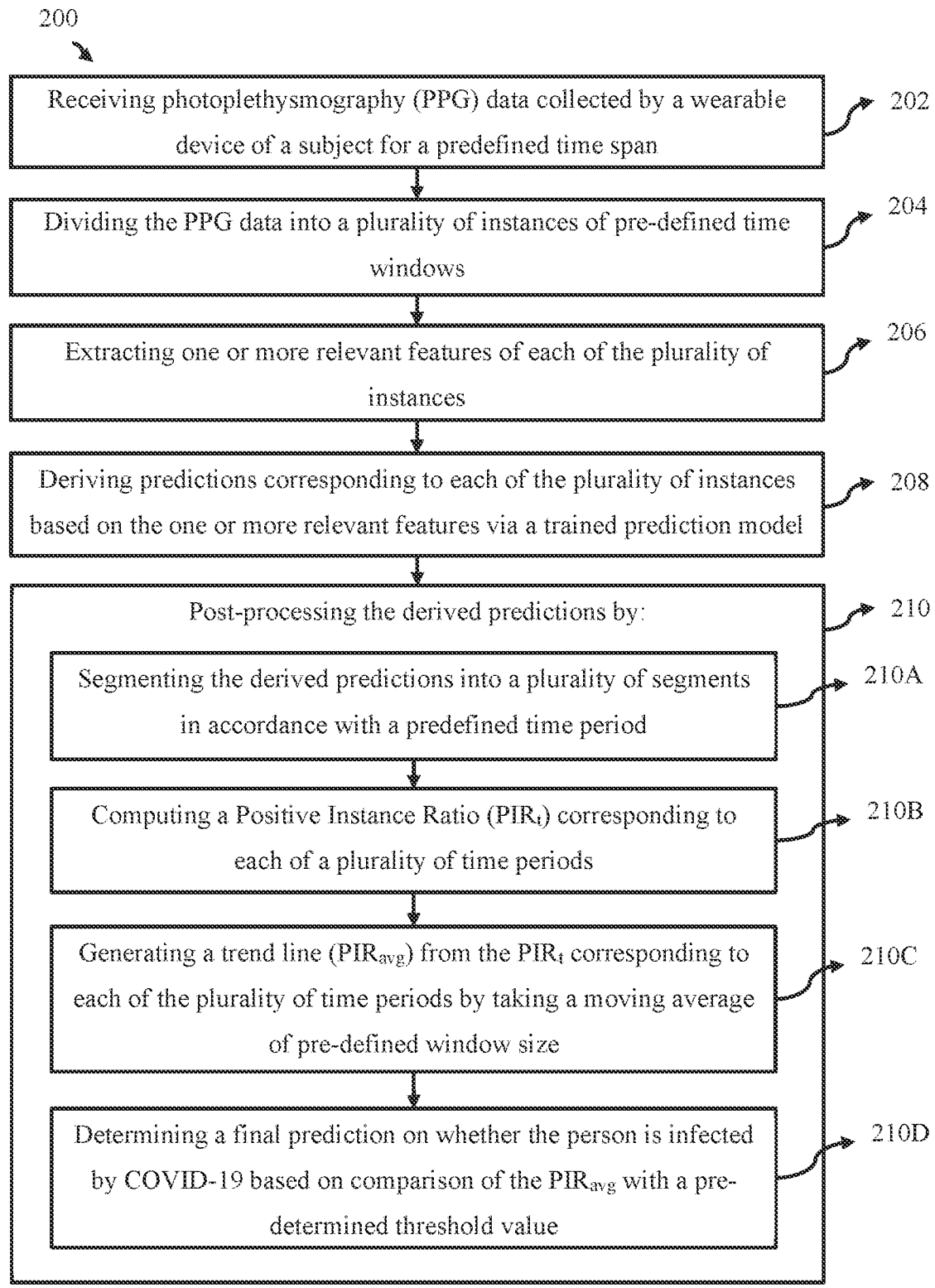
FIG. 2A is a flow diagram illustrating method for early detection of COVID-19, according to some embodiments of the present disclosure.
Figure 2B:
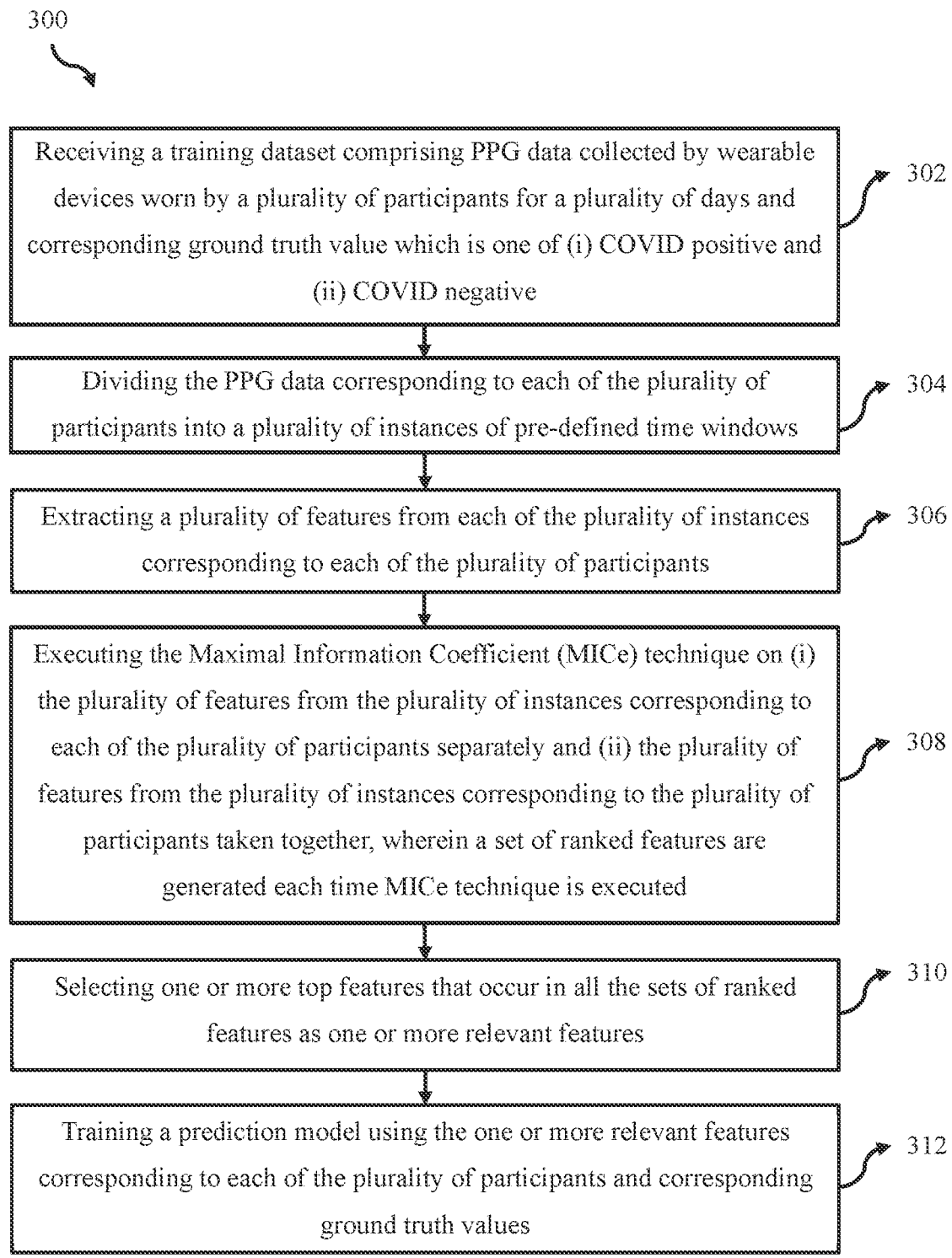
FIG. 2B is a flow diagram illustrating a process of training a prediction model, according to some embodiments of the present disclosure.

In an embodiment, the system 100 comprises one or more data storage devices or the memory 102 operatively coupled to the processor(s) 104 and is configured to store instructions for execution of steps of the method 200 and process 300 depicted in FIGS. 2A and 2B respectively by the processor(s) or one or more hardware processors 104. The steps of the method of the present disclosure will now be explained with reference to the components or blocks of the system 100 as depicted in FIG. 1 and the steps of flow diagrams as depicted in FIGS. 2A and 2B. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIG. 2A is a flow diagram illustrating method 200 for early detection of COVID-19, according to some embodiments of the present disclosure. At step 202 of the method 200, the one or more hardware processors 104 are configured to receive photoplethysmography (PPG) data collected by a wearable device of a subject (alternately referred as participant, user or person and the like) for a predefined time span such as say a plurality of hours. The wearable device is a smartwatch, or any other device equipped with PPG sensor that is able to connect to the network for transferring the data collected from the PPG sensor. The subject has to put on the wearable device for the whole day (24 hours) for effective monitoring and early detection of COVID-19. In an embodiment, the wearable device collects the PPG data continuously and stores it in its internal storage. After a certain time span or when the wearable device is connected to the network or when prompted by the one or more hardware processors 104, the collected data is transferred to the system 100 for further processing. In alternate embodiment, the PPG data collected by the wearable device is continuously transferred to the system 100, which periodically executes the remaining steps of the method 200 for early detection of COVID-19.

Once the PPG data is received, it is pre-processed to remove any noisy or bad sections of the data. Data cleansing technique such as low pass filter with a cutoff frequency at 5 Hz is used to clean up the PPG data before proceeding with prediction analysis. Any other data cleansing/pre-processing techniques may be applied depending on the type of PPG data received. Then, at step 204 of the method 200, the one or more hardware processors 104 are configured to divide the PPG data into a plurality of instances of pre-defined time windows. For example, the PPG data is divided into instances of 5 minute windows. Size of the time window can be configured based on size of the PPG data. Once the PPG data is divided into a plurality of instances, one or more relevant features are extracted from each of the plurality of instances by the one or more hardware processors 104 at step 206 of the method 200. The one or more relevant features are identified during training of the prediction model using Maximal Information Coefficient (MICe) technique followed by final set of features selection. Selection of right features is critical for accurate prediction. The approach followed for feature selection is explained in conjunction with a process 300 illustrated in FIG. 2B. Further, at step 206 of the method 200, predictions corresponding to each of the plurality of instances are derived based on the one or more relevant features via a trained prediction model implemented by the one or more hardware processors 104. The prediction model could be any machine learning classification model such as logistic regression, decision tree, random forest, gradient-boosted tree, and the like. The derived predictions classify whether the participant is COVID positive or COVID negative based on the data in each of the plurality of instances.

Since prediction on just one instance which corresponds to only short time window (for example, 5 minutes) of data from the participant cannot be relied upon, a continuous stream of the predictions over a period of time is taken under consideration. Hence, post processing of the derived predictions is done by the one or more hardware processors 104 at the step 210 to give a final prediction on whether the participant is COVID positive or COVID negative. The post-processing is performed by first segmenting (step 210A) the derived predictions into a plurality of segments in accordance with a predefined time period (say, d hours). Then, at step 210B, a Positive Instance Ratio ($PIR_t$) of the derived predictions is computed for each of the plurality of segments as ratio of a number COVID positive instances in a segment among the plurality of segments to a number of the plurality of instances falling within the segment. Calculation of $PIR_t$ is mathematically expressed according to equation 1.

$$PIR_t = \frac{\text{Number of instances predicted as COVID Positive in a segment}}{\text{Total number of instances in the segment}} \quad (1)$$

Once the PIR values are calculated for the plurality of segments, a trend line ($PIR_{avg}$) is generated at step 210C from the $PIR_t$ corresponding to each of the plurality of segments by taking a moving average of pre-defined window size. For example, trend line $PIR_{avg}$ is generated from $PIR_t$ values by taking a moving average of window size 24 hours and sliding window size of 6 hours. Once the trend line is generated, a final prediction on whether the person is infected by COVID-19 is determined (at step 210D) based on comparison of the $PIR_{avg}$ with a pre-determined threshold value which is determined based on training dataset used for training the prediction model. Firstly, Positive Instance Ratio ($PIR_t$) corresponding to each of the plurality of participants in the training dataset is computed as ratio of number of COVID positive instances to total number of instances in the training dataset. Next, one or more trend line ($PIR_{avg}$) for each of the plurality of participants are generated based on the corresponding $PIR_t$ by using moving average technique. Each of the one or more trend line ($PIR_{avg}$) correspond to one of (i) COVID positive and (ii) COVID negative ground truth value for the corresponding participant. In other words, for each participant one or two $PIR_{avg}$ are generated—one corresponding to COVID positive ground truth and the other corresponding to COVID negative ground truth, whichever is present in the training dataset. Further, mean, and standard deviation of the $PIR_{avg}$ corresponding to COVID positive and COVID negative ground truth value are calculated. Finally, the threshold value is calculated as average of sum of (i) difference of the computed mean and standard deviation of the $PIR_{avg}$ corresponding to COVID positive ground truth value and (ii) sum of the computed mean and standard deviation of the $PIR_{avg}$ corresponding to COVID negative ground truth value according to equation 2.

$$\frac{(\text{mean} + \text{standard\_deviation})_{COVID\ positive} + (\text{mean} + \text{standard\_deviation})_{COVID\ negative}}{2} \quad (2)$$

FIG. 2B is a flow diagram illustrating the process 300 of training the prediction model, according to some embodiments of the present disclosure. At step 302 of the process 300, one or more hardware processors 104 are configured to receive a training dataset comprising PPG data collected by wearable devices worn by a plurality of participants for a plurality of days and corresponding ground truth value which is one of (i) COVID positive and (ii) COVID negative. The ground truth value may be determined by standard test such as RT-PCR. Further, at step 302 of the process 300, one or more hardware processors 104 are configured to divide the PPG data corresponding to each of the plurality of participants into a plurality of instances of pre-defined time windows (for example, 5 minutes). The time window can be specified by an expert based on size of PPG data in the training dataset. Further, at step 306 of the process 300, one or more hardware processors 104 are configured to extract a plurality of features from each of the plurality of instances corresponding to each of the plurality of participants. The plurality of features can be extracted using any state of the art feature extraction tool such as feature discovery platform (Indian patent application number 201821022092). Practically, calculating all the features of PPG data corresponding to all the subjects take a lot of time and consumes significant resources of the system 100 (memory and processing power). It is desirable to identify a subset of features which are relevant to all the subjects and also doesn't significantly affect accuracy of final prediction. Hence, steps 308 and 310 are implemented to identify one or more relevant features. It has been experimentally identified that although accuracy of prediction model slightly reduces when subset of features are used instead of the plurality of features, it doesn't affect the end result since prediction across multiple days is considered for final prediction.

Returning to process 300, at step 308 the one or more hardware processors 104 are configured to execute Maximal Information Coefficient (MICe) technique on (i) the plurality of features from the plurality of instances corresponding to each of the plurality of participants separately and (ii) the plurality of features from the plurality of instances corresponding to the plurality of participants taken together. A set of ranked features are generated each time MICe technique is executed. For example, if there are N participants, MICe algorithm is executed separately on features extracted from PPG data of each of the N participants and then MICe algorithm is executed on all the features extracted from PPG data of all the N participants. Thus, N+1 sets of ranked features are obtained. Further, at step 310, one or more top features that occur in all the sets of ranked features are selected as one or more relevant features. The ranked set of features show important features for different data collected from different participants. Taking intersection of the ranked set of features enables selecting best features among them which are relevant to data collected from all the participants and therefore helps in deriving right predictions.

Once the one or more relevant features are identified, at step 312 of the process 300, the one or more hardware processors 104 are configured to train the prediction model using the one or more relevant features corresponding to each of the plurality of participants and corresponding ground truth values. The trained model can then be used in method 200 for early detection of COVID-19 in a subject.

EXPERIMENTAL RESULTS

The experiments were conducted in coordination with a hospital in India that had an active COVID-19 ward to conduct a study on health care workers involved in management of COVID-19. The study was registered as a cross sectional type observational trial at the Clinical Trials Registry-India (CTRI), approved by the ethical committee at the hospital and conducted on volunteers in the age group of 19 to 60. All the volunteers signed an informed consent before participation. Most modern fitness trackers and smart watches such as the Fitbit or the Samsung Galaxy Gear include sensors such as the photoplethysmography (PPG) and inertial measurement unit (IMU) that assist in computing metrics such as the heart rate and activity level. For the experiments, Empatica E4 was used primarily for its high level of data integrity. The list of sensors available on the device and the set of measures derived from them are highlighted in Table 1. The data available from this device are PPG at 64 Hz, electrodermal activity (EDA) at 4 Hz, 3-axis accelerometer at 32 Hz, heart rate (HR) at 4 Hz and temperature data at 1 hz. In an embodiment, these measures can be displayed to a user via the I/O interface.

TABLE 1

| Sensor | Derived Measure |
|---|---|
| PPG | Hourly heart rate (HR) - Estimated instantaneous HR averaged over the hour |
| PPG | Hourly resting heart rate - Average heart rate of 5 minutes post a 10 minute rest detection. |
| PPG | Hourly respiratory rate (RR) - Estimated instantaneous respiratory rate averaged over the hour |
| Infrared Thermopile | Average skin temperature for the hour |
| IMU | Cumulative step-count of the hour |
| EDA sensor | To detect removal of the wearable device |

The pilot study, that started in the mid-week of June 2020, involved 10 healthcare professionals (7 doctors, 2 nurses, 1 Technician) treating COVID patients. The device was worn for 24 hours (including during their 8-12 hour shifts) a day, except when there is some discomfort or during use of washroom/shower, with data synchronization and device charging/sanitization occurring prior to the start of their shift. At the time of onboarding, data such as blood pressure, body temperature (Axilla), oxygen saturation ($SpO_2$) and heart rate are captured using medical grade device to serve as a baseline measure. To maintain data privacy, the hospital staff handled mapping of device to participant and only a user ID is stored in the database. Given the restriction of carrying a mobile device during their shift, and in particular within the COVID ward, the E4 device operates in 'record' mode where data is stored locally on the device and later synchronized offline to the Empatica cloud. The data is then downloaded to and processed on system 100. The measures listed in Table 1 and prediction made using the method 200 are displayed to hospital staff via the I/O interface 106.

Data was collected as 4 cohorts (Table 2 and Table 3), with different participants (healthcare workers) in each cohort. The same device is not used for more than one user ID in a given cohort. All the data were recorded on the device itself, which were pulled and synced to the database at the end of the day. Extra care was taken to ensure the device is worn firmly on the wrist and should remain in contact with the skin for accurate PPG measurements. PPE kit was worn above the device. For cohort 1, (user IDs C1-USRxxx) 20 participants signed up for the experiment. But due to non-compliance (not wearing the watch or not following the protocol), limited data was found to be usable. Ultimately data for user IDs 3, 6, 16 and 18 were used as the top 4 participants with respect to duration of data provided. Data collection for cohort 2 (user ids C2-USRxxx) lasted for approximately 15 days. In this cohort 6 participants participated but out of 6, data from only 4 participants turned out to be useful. RT-PCR tests were conducted for the 4 participants at the end of the cohort which resulted in 2 participants being tested COVID-19 positive (COV+) and other 2 COVID-19 negative (COV-). For Cohort 3 (C3) comprising 8 participants, data was collected in the same way and RT-PCR test was conducted regularly to evaluate the participants for any infection. Cohort 4 (C4) included 7 participants some of whom were infected while some were not based on RT-PCR test. The results of RT-PCR test for both C3 and C4 were not revealed to the researchers making it a double blind test. Once the data analysis was completed, the predictions for C3 and C4 were compared with the RT-PCR results for validation. The RT-PCR test results are considered as ground truth.

TABLE 2

| Cohort | Start date | End date |
|---|---|---|
| Cohort 1 (C1) | 15 Jun. 2020 | 16 Jul. 2020 |
| Cohort 2 (C2) | 21 Jul. 2020 | 7 Aug. 2020 |
| Cohort 3 (C3) | 27 Jan. 2021 | 21 Feb. 2021 |
| Cohort 4 (C4) | 19 Apr. 2021 | 5 May 2021 |

TABLE 3

| User ID | Number of days | Duration (in hours) | Ground truth |
|---|---|---|---|
| C1-USR001 | 3 | 0.657 | COV- |
| C1-USR002 | 0 | 0 | COV- |
| C1-USR003 | 18 | 265.880 | COV- |
| C1-USR004 | 4 | 2.571 | COV- |
| C1-USR005 | 2 | 20.228 | COV- |
| C1-USR006 | 12 | 193.198 | COV- |
| C1-USR007 | 10 | 35.563 | COV- |
| C1-USR008 | 1 | 0.843 | COV- |
| C1-USR009 | 6 | 9.127 | COV- |
| C1-USR010 | 1 | 0.005 | COV- |
| C1-USR011 | 10 | 22.473 | COV- |
| C1-USR012 | 11 | 10.438 | COV- |
| C1-USR015 | 8 | 17.410 | COV- |
| C1-USR016 | 8 | 121.680 | COV- |
| C1-USR017 | 11 | 95.260 | COV- |
| C1-USR018 | 13 | 186.722 | COV- |
| C1-USR019 | 14 | 155.093 | COV- |
| C1-USR020 | 2 | 32.113 | COV- |
| C2-USR021 | 12 | 99.22 | COV+ |
| C2-USR024 | 12 | 123.6 | COV+ |
| C2-USR019 | 14 | 177.37 | COV- |
| C2-USR022 | 7 | 68.93 | COV- |
| C2-USR025 | 13 | 278.51 | COV- |
| C3-USR001 | 15 | 257.53 | COV- |
| C3-USR003 | 12 | 137.31 | COV- |
| C3-USR004 | 15 | 264.54 | COV- |
| C3-USR006 | 12 | 172.42 | COV- |
| C3-USR007 | 8 | 84.07 | COV- |
| C3-USR009 | 15 | 258.13 | COV- |
| C3-USR011 | 8 | 115.15 | COV- |
| C3-USR012 | 5 | 82.38 | COV- |
| C4-USR001 | 6 | 82.477 | COV+ |
| C4-USR002 | 6 | 183.634 | COV+ |
| C4-USR003 | 5 | 97.875 | COV+ |
| C4-USR004 | 5 | 89.858 | COV- |
| C4-USR005 | 5 | 167.748 | COV+ |
| C4-USR006 | 11 | 220.117 | COV- |
| C4-USR009 | 11 | 216.993 | COV- |

From the above collected data, the PPG signal is used to build the prediction model such that, the generated model can be used to classify whether new incoming data is from a healthy participant or not. Training data used for training the prediction model is Cohort 2 data, which comprises 2 participants who were infected with COVID-19 during the process of data collection. Each participant's data was divided into training and test dataset using 80-20 split criteria. 80% instances of each day is taken as training dataset (referred as C2-Train) and 20% of each day data is taken as test dataset (referred as C2-Test). The average duration of data obtained from each participant was approximately 100 hours across 15 days. Given the size of the data, a window size of 5 mins was chosen for analysis of the PPG signal. The raw data is pre-processed to remove any noisy or bad sections of the data. The conditioned signal is then divided into a plurality of instances of 5 minute windows. Each of the plurality of instances is then fed to a tool called Feature discovery platform (Indian patent application number 201821022092), which returns a set of 392 features comprising time domain, frequency domain, wavelet transformed derivatives and hurst components. Once the features are extracted, a prediction model was trained using the training dataset. Experiments were carried out by training different machine learning models, among them Random Forest classifier with 100 trees gave optimum results for different combination. Using all the 392 features, an accuracy of 89.9% was obtained on C2-Test and 74.5% cohort 1 data (referred as C1-Test). Then, feature selection was performed by executing MICe for each participant separately as well as all participants combined, and the list of top 50 features is obtained from all the 5 runs (4 participants and 1 all participants combined). Next, intersection of the features obtained in all the 5 lists are taken to get 15 features (listed in Table 4). The prediction model trained on this set of 15 features gave an accuracy of 84.8% on C2-Test data. Table 5 reports various metrics calculated on the trained model. It is observed that there is a drop in the accuracy when the features are reduced. On the other hand, computation is significantly faster and therefore enables predictions for a larger number of participants. Since the prediction model gives prediction on a daily basis, based on the entire day's data and a longitudinal threshold, marginal variation in accuracy will not affect the final prediction. The threshold value calculated for the training data was 0.6. Thus, if the participant's PIR values was greater than 0.6 on a certain day or for number of days, then, the patient is COVID positive during those days.

Figure 3:
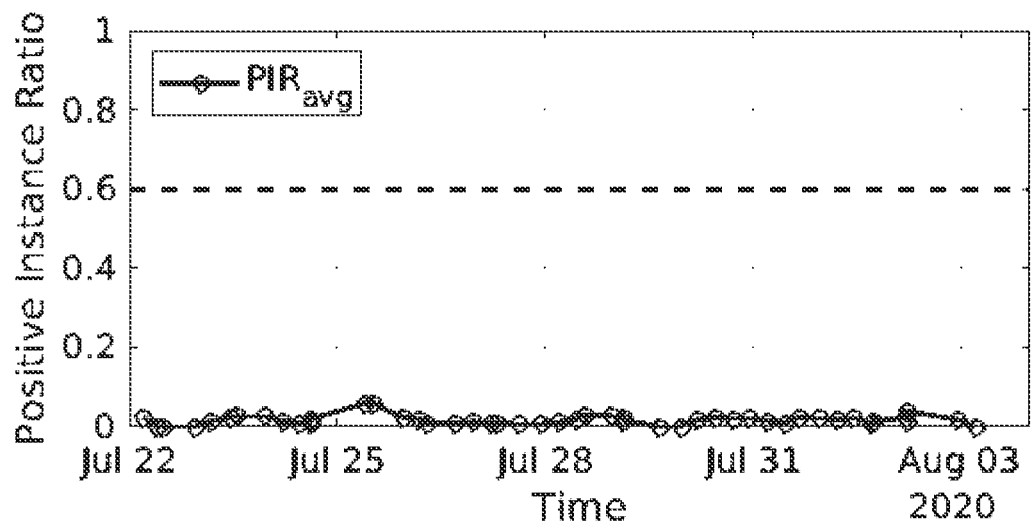
FIG. 3 is a Positive Instance Ratio (PIR) plot corresponding to a COVID negative participant in a second cohort, according to some embodiments of the present disclosure.
Figure 4:
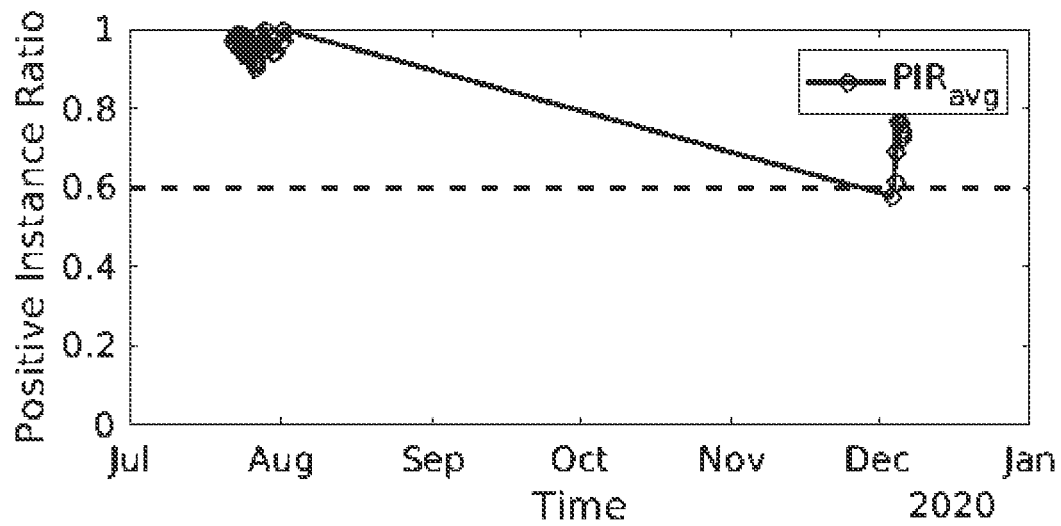
FIG. 4 is a PIR plot corresponding to a COVID positive participant in the second cohort, according to some embodiments of the present disclosure.
Figure 5:
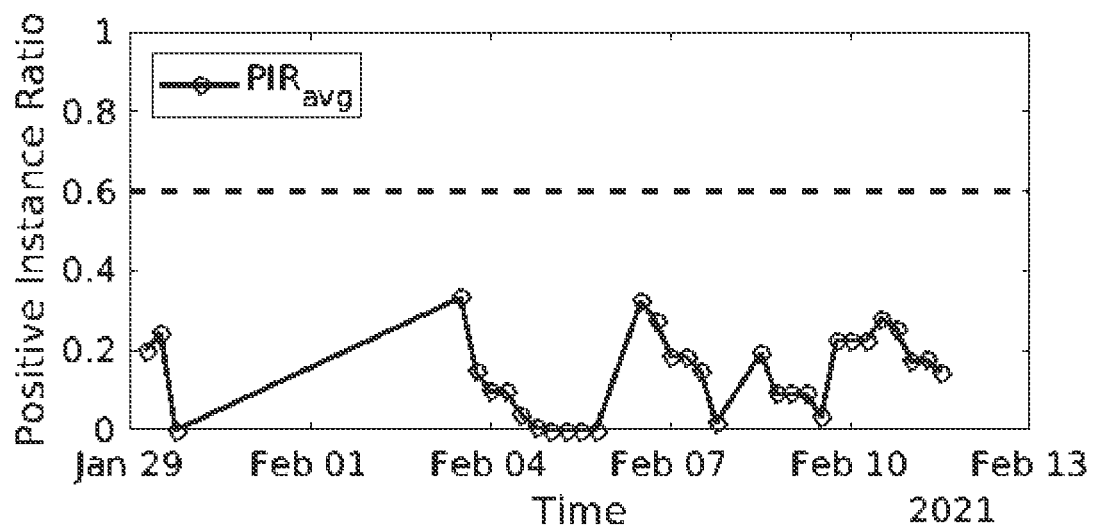
FIG. 5 is a PIR plot corresponding to a COVID negative participant in a third cohort, according to some embodiments of the present disclosure.
Figure 6:
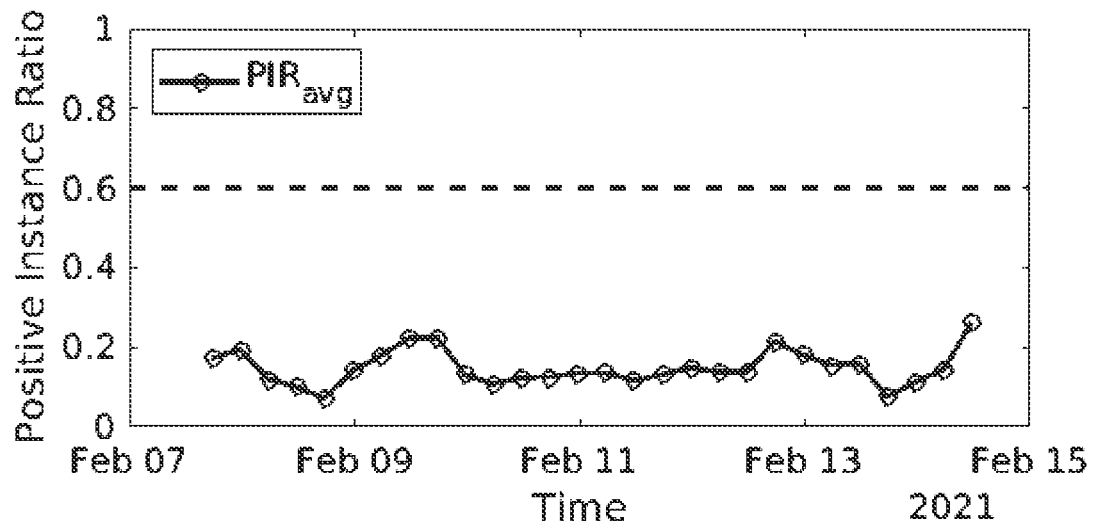
FIG. 6 is a PIR plot corresponding to a COVID negative participant in the third cohort, according to some embodiments of the present disclosure.
Figure 7:
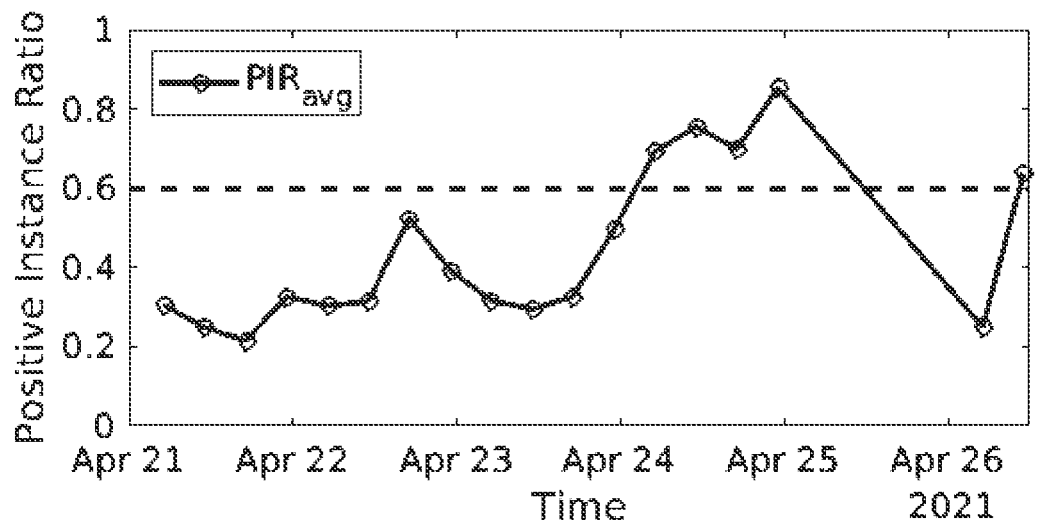
FIG. 7 is a PIR plot corresponding to a COVID positive participant in a fourth cohort, according to some embodiments of the present disclosure.
Figure 8:
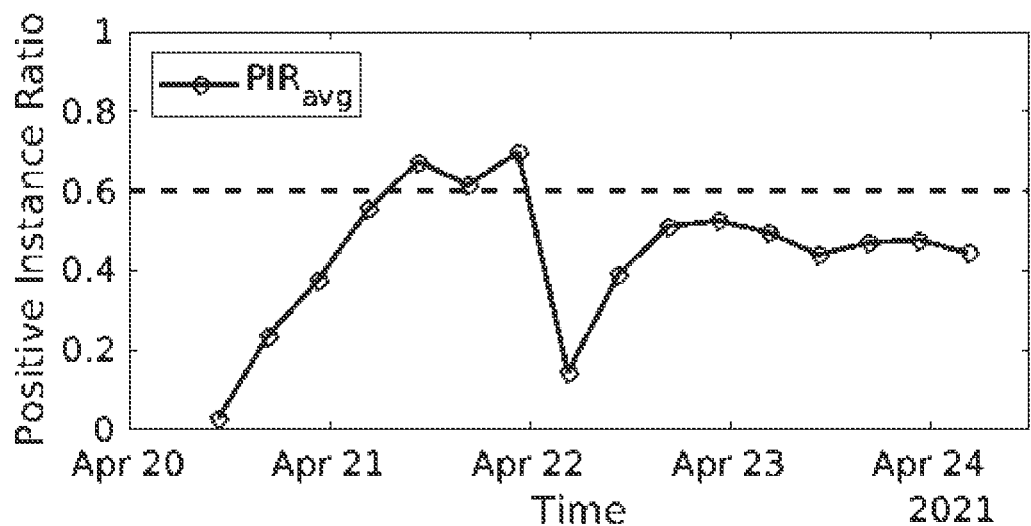
FIG. 8 is a PIR plot corresponding to a COVID positive participant in the fourth cohort, according to some embodiments of the present disclosure.

FIGS. 3 and 4 show the PIR plots for two participants under study. For C2-USR019 (FIG. 3), who was COV– throughout the study, has a PIR constantly below the threshold of 0.6. On the other hand, for C2-USR021 (FIG. 4), who was infected during the study, has a PIR plot above 0.6 in the date range of July-August 2020. Further, to validate the method 200, additional data was collected from participants 21 and 24 during December 2020. Assuming the participants have recovered completely, the method 200 was implemented on the collected data to obtain the corresponding predictions and PIR plots. As illustrated in FIG. 4, PIR values drop during the timeline of December 2020, further confirming that the trained model is working correctly. The prediction model was again tested using data from Cohort 3 and Cohort 4. The results of the corresponding RT-PCR test (ground truth) were not made available to the researchers apriori making it a double blind test. PIR plots were obtained using the method 200. FIGS. 5 and 6 illustrate the PIR plots for 2 participants where it can be seen that the values remain below the threshold of Hence, it can be concluded that all the participants of Cohort 3 are COV–. Later the corresponding results of RT-PCR test was made available where all the participants were reported as COV–, matching the predictions from the method 200. Being frontline workers, all the cohort 3 participants were vaccinated and hence did not contract the infection. Similarly for Cohort 4, the prediction made by the method 200 are listed in Table 6 and the PIR plots for participant 1 and participant 5 are illustrated in FIGS. 7 and 8 respectively. Out of the 7 participants, the method 200 predicted 3 as COV+ and 3 as COV– and one as suspected/mostly COV+. When the RT-PCR results were revealed, 4 subjects (including the one predicted as suspected COV+) turned out to be COV+ and the remaining 3 COV–, matching the predictions.

TABLE 4

| Features |
| --- |
| ZeroCrossingRate of TD |
| Mean of windowedZeroCrossingRate of TD |
| Mean of windowedZeroCrossingRate of DWT (a1) |
| ZeroCrossingRate of DWT (a1) |
| Mean of windowedZeroCrossingRate of DWT (a2) |
| ZeroCrossingRate of DWT (a2) |
| Mean of windowedZeroCrossingRate of DWT (d2) |
| ZeroCrossingRate of DWT (d2) |
| Mean of windowedBox-PierceStat3 of TD |
| FFT_Energy_80PC |
| Mean of windowedBox-PierceStat2 of DWT (a1) |
| Mean of windowedHurstExponentEstimate of DWT (a2) |
| Mean of windowedHurstExponentEstimate of DWT (a3) |
| Mean of windowedHurstExponentEstimate of DWT (a1) |
| Windowed_FFT_Spectral_rolloff_mean |

TABLE 6

| User ID | Ground Truth | Prediction from method 200 |
| --- | --- | --- |
| C4-USR001 | COV+ | COV+ |
| C4-USR002 | COV+ | Suspected COV+ |
| C4-USR003 | COV+ | COV+ |
| C4-USR004 | COV– | COV– |
| C4-USR005 | COV+ | COV+ |
| C4-USR006 | COV– | COV– |
| C4-USR009 | COV– | COV– |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from

TABLE 5

| Train data | Test data | Number of features | Accuracy | Sensitivity | Specificity | Precision | Recall |
| --- | --- | --- | --- | --- | --- | --- | --- |
| C2-train | C2-test | 392 | 0.8998 | 0.7862 | 0.9545 | 0.8931 | 0.7862 |
| C2-train | C1-test | 392 | 0.7453 | NA* | 0.74539 | NA* | NA* |
| C2-train | C2-test | 15 | 0.8481 | 0.7117 | 0.9139 | 0.7995 | 0.7117 |

*NA: Not Applicable as C1-Test had only one class data (COV–)

the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:
   receiving, via one or more hardware processors, photoplethysmography (PPG) data collected by a wearable device of a subject for a predefined time span;
   dividing, via the one or more hardware processors, the PPG data into a plurality of instances of pre-defined time windows;
   extracting, via the one or more hardware processors, one or more relevant features of each of the plurality of instances, wherein the one or more relevant features are identified during training phase using a Maximal Information Coefficient (MICe) technique;
   deriving predictions corresponding to each of the plurality of instances based on the one or more relevant features via a trained prediction model implemented by the one or more hardware processors, wherein the derived predictions are one of: (i) COVID positive and (ii) COVID negative; and
   post-processing, via the one or more hardware processors, the derived predictions by:
      segmenting the derived predictions into a plurality of segments in accordance with a predefined time period;
      computing a Positive Instance Ratio ($PIR_t$) of the derived predictions for each of the plurality of segments, wherein the $PIR_t$ is ratio of a number COVID positive instances in a segment among the plurality of segments to a number of the plurality of instances falling within the segment;
      generating a trend line ($PIR_{avg}$) from the $PIR_t$ corresponding to each of the plurality of segments by taking a moving average of pre-defined window size; and
      determining a final prediction on whether the subject is COVID-19 positive based on comparison of the $PIR_{avg}$ with a pre-determined threshold value;
   wherein the prediction model is trained by:
      receiving a training dataset comprising PPG data collected by wearable devices worn by a plurality of participants for a plurality of days and corresponding ground truth value which is one of (i) COVID positive and (ii) COVID negative;
      dividing the PPG data corresponding of the plurality of participants into a plurality of instances of pre-defined time windows;
      extracting a plurality of features from each of the plurality of instances corresponding to each of the plurality of participants;
      executing the Maximal Information Coefficient (MICe) technique on (i) the plurality of features from the plurality of instances corresponding to each of the plurality of participants separately and (ii) the plurality of features from the plurality of instances corresponding to the plurality of participants taken together, wherein a set of ranked features are generated each time MICe technique is executed;
selecting one or more top features that occur in all the sets of ranked features as one or more relevant features; and
training a prediction model using the one or more relevant features corresponding to each of the plurality of participants and corresponding ground truth values,
wherein the threshold value is determined by:
computing a Positive instance Ratio ($PIR_t$) corresponding to each of the plurality of pants in the training dataset, wherein $PIR_t$ is ratio of number of COVID positive instances to total number of instances in the training dataset,
generating one or more trend line ($PIR_{avg}$) for each of the plurality of participants based on the corresponding $PIR_t$ by using moving average technique, wherein each of the one or more trend line ($PIR_{avg}$) correspond to one of (i) COVID positive and (ii) COVID negative ground truth value for the corresponding participant;
computing mean and standard deviation of the $PIR_{avg}$ corresponding to COVID positive and COVID negative ground truth value; and
calculating the threshold value as average of sum of (i) difference of the computed mean and standard deviation of the $PIR_{avg}$ corresponding to COVID positive ground truth value and (ii) sum of the computed mean and standard deviation of the $PIR_{avg}$ corresponding to COVID negative ground truth value.

2. A system comprising:
a memory storing instructions;
one or more communication interfaces; and
one or more hardware processors coupled to the memory via the one or more communication interfaces, wherein the one or more hardware processors are configured by the instructions to:
receive photoplethysmography (PPG) data collected by a wearable device of a subject for a predefined time span;
divide the PPG data into a plurality of instances of pre-defined time windows;
extract one or more relevant features of each of the plurality of instances, wherein the one or more relevant features are identified during training phase using a Maximal Information Coefficient (MICe) technique;
derive predictions corresponding to each of the plurality of instances based on the one or more relevant features via a trained prediction model implemented by the one or more hardware processors, wherein the derived predictions are one of:
(i) COVID positive and (ii) COVID negative; and
post-process the derived predictions by:
segmenting the derived predictions into a plurality of segments in accordance with a predefined time period;
computing a Positive Instance Ratio ($PIR_t$) of the derived predictions for each of the plurality of segments, wherein the $PIR_t$ is ratio of a number COVID positive instances in a segment among the plurality of segments to a number of the plurality of instances falling within the segment;
generating a trend line ($PIR_{avg}$) from the $PIR_t$ corresponding to each of the plurality of segments by taking a moving average of pre-defined window size; and
determining a final prediction on whether the subject is COVID-19 positive based on comparison of the $PIR_{avg}$ with a pre-determined threshold value;
wherein the one or more hardware processors are configured to train the prediction model by:
receiving a training dataset comprising PPG data collected by wearable devices worn by a plurality of participants for a plurality of days and corresponding ground truth value which is one of (i) COVID positive and (ii) COVID negative;
dividing the PPG data corresponding to each of the plurality of participants into a plurality of instances of pre-defined time windows;
extracting a plurality of features from each of the plurality of instances corresponding to each of the plurality of participants;
executing the Maximal Information Coefficient (MICe) technique on (i) the plurality of features from the plurality of instances corresponding to each of the plurality of participants separately and (ii) the plurality of features from the plurality of instances corresponding to the plurality of participants taken together, wherein a set of ranked features are generated each time MICe technique is executed;
selecting one or more top features that occur in all the sets of ranked features as one or more relevant features; and
training a prediction model using the one or more relevant features corresponding to each of the plurality of participants and corresponding ground truth values;
wherein the threshold value is determined by:
computing a Positive Instance Ratio ($PIR_t$) corresponding to each of the plurality of participants in the training dataset, wherein $PIR_t$ is ratio of number of COVID positive instances to total number of instances in the training dataset;
generating one or more trend line ($PIR_{avg}$) for each of the plurality of participants based on the corresponding $PIR_t$ by using moving average technique, wherein each of the one or more trend line ($PIR_{avg}$) correspond to one of (i) COVID positive and (ii) COVID negative ground truth value for the corresponding participant;
computing mean and standard deviation of the $PIR_{avg}$ corresponding to COVID positive and COVID negative ground truth value, and
calculating the threshold value as average of sum of (i) difference of the computed mean and standard deviation of the $PIR_{avg}$ corresponding to COVID positive ground truth value and (ii) sum of the computed mean and standard deviation of the $PIR_{avg}$ corresponding to COVID negative ground truth value.

3. One or more non-transitory machine-readable information storage mediums comprising one or more instructions which when executed by one or more hardware processors cause:
receiving photoplethysmography (PPG) data collected by a wearable device of a subject for a predefined time span;
dividing the PPG data into a plurality of instances of pre-defined time windows;
extracting one or more relevant features of each of the plurality of instances, wherein the one or more relevant features are identified during training phase using a Maximal Information Coefficient (MICe) technique;
deriving predictions corresponding to each of the plurality of instances based on the one or more relevant features via a trained prediction model wherein the derived predictions are one of: (i) COVID positive and (ii) COVID negative; and post-processing the derived predictions by:
  segmenting the derived predictions into a plurality of segments in accordance with a predefined time period;
  computing a Positive Instance Ratio ($PIR_t$) of the derived predictions for each of the plurality of segments, wherein the $PIR_t$ is ratio of a number COVID positive instances in a segment among the plurality of segments to a number of the plurality of instances falling within the segment;
  generating a trend line ($PIR_{avg}$) from the $PIR_t$ corresponding to each of the plurality of segments by taking a moving average of pre-defined window size; and
  determining a final prediction on whether the subject is COVID-19 positive based on comparison of the $PIR_{avg}$ with a pre-determined threshold value;

wherein the prediction model is trained by:
  receiving a training dataset comprising PPG data collected by wearable devices worn by a plurality of participants for a plurality of days and corresponding ground truth value which is one of (i) COVID positive and (ii) COVID negative;
  dividing the PPG data corresponding to each of the plurality of participants into a plurality of instances of pre-defined time windows;
  extracting a plurality of features from each of the plurality of instances corresponding to each of the plurality of participants;
  executing the Maximal Information Coefficient (MICe) technique on (i) the plurality of features from the plurality of instances corresponding to each of the plurality of participants separately and (ii) the plurality of features from the plurality of instances corresponding to the plurality of participants taken together, wherein a set of ranked features are generated each time MICe technique is executed;
  selecting one or more top features that occur in all the sets of ranked features as one or more relevant features; and
  training a prediction model using the one or more relevant features corresponding to each of the plurality of participants and corresponding ground truth values;

wherein the threshold value is determined by:
  computing a Positive Instance Ratio ($PIR_t$) corresponding to each of the plurality of participants in the training dataset, wherein $PIR_t$ is ratio of number of COVID positive instances to total number of instances in the training dataset;
  generating one or more trend line ($PIR_{avg}$) for each of the plurality of participants based on the corresponding $PIR_t$ by using moving average technique, wherein each of the one or more trend line ($PIR_{avg}$) correspond to one of (i) COVID positive and (ii) COVID negative ground truth value for the corresponding participant,
  computing mean and standard deviation of the $PIR_{avg}$ corresponding to COVID positive and COVID negative ground truth value; and
  calculating the threshold value as average of sum of (i) difference of the computed mean and standard deviation of the $PIR_{avg}$ corresponding, to COVID positive ground truth value and (ii) sum of the computed mean and standard deviation of the $PIR_{avg}$ corresponding to COVID negative ground truth value.

* * * * *